(12) United States Patent
Ben Nun

(10) Patent No.: US 11,540,915 B2
(45) Date of Patent: Jan. 3, 2023

(54) HANDHELD IMPLANTATION DEVICES FOR IMPLANTATION OR RETINAL TISSUE IMPLANT

(71) Applicant: E.K.—D.D.S. LTD., Tel Aviv (IL)

(72) Inventor: Joshua Ben Nun, Beit Herut (IL)

(73) Assignee: E.K.—D.D.S. LTD., Tel Aviv (IL)

( * ) Notice: Subject to any disclaimer, the term of this patent is extended or adjusted under 35 U.S.C. 154(b) by 0 days.

(21) Appl. No.: 16/764,972

(22) PCT Filed: Nov. 18, 2018

(86) PCT No.: PCT/IL2018/051241
§ 371 (c)(1),
(2) Date: May 18, 2020

(87) PCT Pub. No.: WO2019/102455
PCT Pub. Date: May 31, 2019

(65) Prior Publication Data
US 2020/0323625 A1    Oct. 15, 2020
US 2022/0354634 A9    Nov. 10, 2022

Related U.S. Application Data

(63) Continuation-in-part of application No. 16/501,078, filed on Feb. 19, 2019, now Pat. No. 11,065,106, (Continued)

(30) Foreign Application Priority Data

Jan. 21, 2014  (IL) .......................................... 230567
Nov. 21, 2017  (IL) .......................................... 255796

(51) Int. Cl.
*A61F 2/14* (2006.01)
*A61F 9/007* (2006.01)
*A61N 1/05* (2006.01)

(52) U.S. Cl.
CPC .......... *A61F 2/148* (2013.01); *A61F 9/00727* (2013.01); *A61F 2210/0071* (2013.01); *A61N 1/0543* (2013.01)

(58) Field of Classification Search
CPC ............................. A61F 2/148; A61F 9/00727
See application file for complete search history.

(56) References Cited

U.S. PATENT DOCUMENTS 3,911,925 A  *  10/1975  Tillery, Jr. ................ A61D 1/04
                                                            606/208
5,098,439 A     3/1992  Hill et al.
(Continued)

FOREIGN PATENT DOCUMENTS

CN         101495063         7/2009
EP         1472986 A1       11/2004
(Continued)

OTHER PUBLICATIONS

The International Bureau of WIPO, International Preliminary Report on Patentability for PCT/SI2018/051241, dated May 26, 2020.
(Continued)

*Primary Examiner* — Javier G Blanco
(74) *Attorney, Agent, or Firm* — Robert G. Lev

(57) ABSTRACT

A handheld implantation device for implantation of a retinal tissue implant at an implantation site. The handheld implantation device includes a handheld implantation tool having a leading implantation tool end and a trailing implantation tool end, an implant holder for peripherally holding a retinal tissue implant including an uppermost viable retinal tissue and a lowermost basement membrane and a clinician-operated attachment arrangement for initial attaching the implant holder at the leading implantation tool end and subsequent selected detaching the implant holder therefrom at the
(Continued)

implantation site for implantation of the implant holder together with the retinal tissue implant thereat.

5 Claims, 7 Drawing Sheets

Related U.S. Application Data which is a continuation of application No. 15/111,996, filed as application No. PCT/IL2015/050049 on Jan. 14, 2015, now Pat. No. 10,251,747.

(56) References Cited

U.S. PATENT DOCUMENTS

| | | | |
|---|---|---|---|
| 8,470,029 B2 | 6/2013 | Walter et al. | |
| 10,251,747 B2 | 4/2019 | Ben Nun et al. | |
| 2006/0173539 A1 | 8/2006 | Shiuey | |
| 2007/0208422 A1* | 9/2007 | Walter | A61F 9/007 623/5.11 |
| 2007/0282131 A1 | 12/2007 | Stauffer | |
| 2008/0281341 A1 | 11/2008 | Miller et al. | |
| 2010/0211051 A1 | 8/2010 | Weston et al. | |
| 2012/0059488 A1 | 3/2012 | Shimmura | |
| 2012/0245592 A1 | 9/2012 | Berner et al. | |
| 2013/0085567 A1* | 4/2013 | Tan | A61F 2/148 623/5.12 |
| 2013/0123916 A1 | 5/2013 | Nigam | |
| 2013/0253529 A1 | 9/2013 | Walter et al. | |
| 2015/0032207 A1* | 1/2015 | Humayun | A61F 9/00736 623/23.72 |
| 2019/0223997 A1 | 7/2019 | Ben Nun et al. | |

FOREIGN PATENT DOCUMENTS

| | | | |
|---|---|---|---|
| EP | 1981437 | 10/2008 | |
| EP | 2601996 A1 | 6/2013 | |
| JP | 2009524486 | 7/2009 | |
| JP | 5312951 | 10/2013 | |
| WO | WO 1994/21205 A1 | 9/1994 | |
| WO | WO 2000/76403 A1 | 12/2000 | |
| WO | WO 2007089508 | 8/2007 | |
| WO | WO 2007132332 | 11/2007 | |
| WO | WO 2007143111 | 12/2007 | |
| WO | WO 2012/149468 A2 | 11/2012 | |
| WO | WO-2012149468 A2 * | 11/2012 | A61B 17/2909 |
| WO | WO 2014049591 | 4/2014 | |
| WO | WO-2014049591 A1 * | 4/2014 | A61B 18/08 |
| WO | WO 2015/111040 A1 | 7/2015 | |

OTHER PUBLICATIONS

European Patent Office, Extended European Search Report for PCT/IL2015/050049, dated Sep. 26, 2017.

William J. Reinhart et al., Deep Anterior Lamellar Keratoplasty as an Alternative to Penetrating Keratoplasty. Ophthalmology vol. 118, No. 1, pp. 209-218, Jan. 2011, doi:10.1016/j.ophtha.2010.11.002.

John Thomas, Corneal Endothlial Transplant (DSAEK, DMEK & DLEK), Section 4 Surgical Instruments,pp. 108-119, table 11-1. Jaypee Brothers Medical Publishers Ltd, 2010 . . . www.google.co.il/books?hl=en&lr=&id=LrJH35GlxO0C&oi=fnd&pg=PAI&dq=corneal+edothelial+thomas+John&ots=JHLLgKQtyK& sig=VuPeQGEtE8nYd6GHhpCS23DpTuw&redir_esc=y.

\* cited by examiner

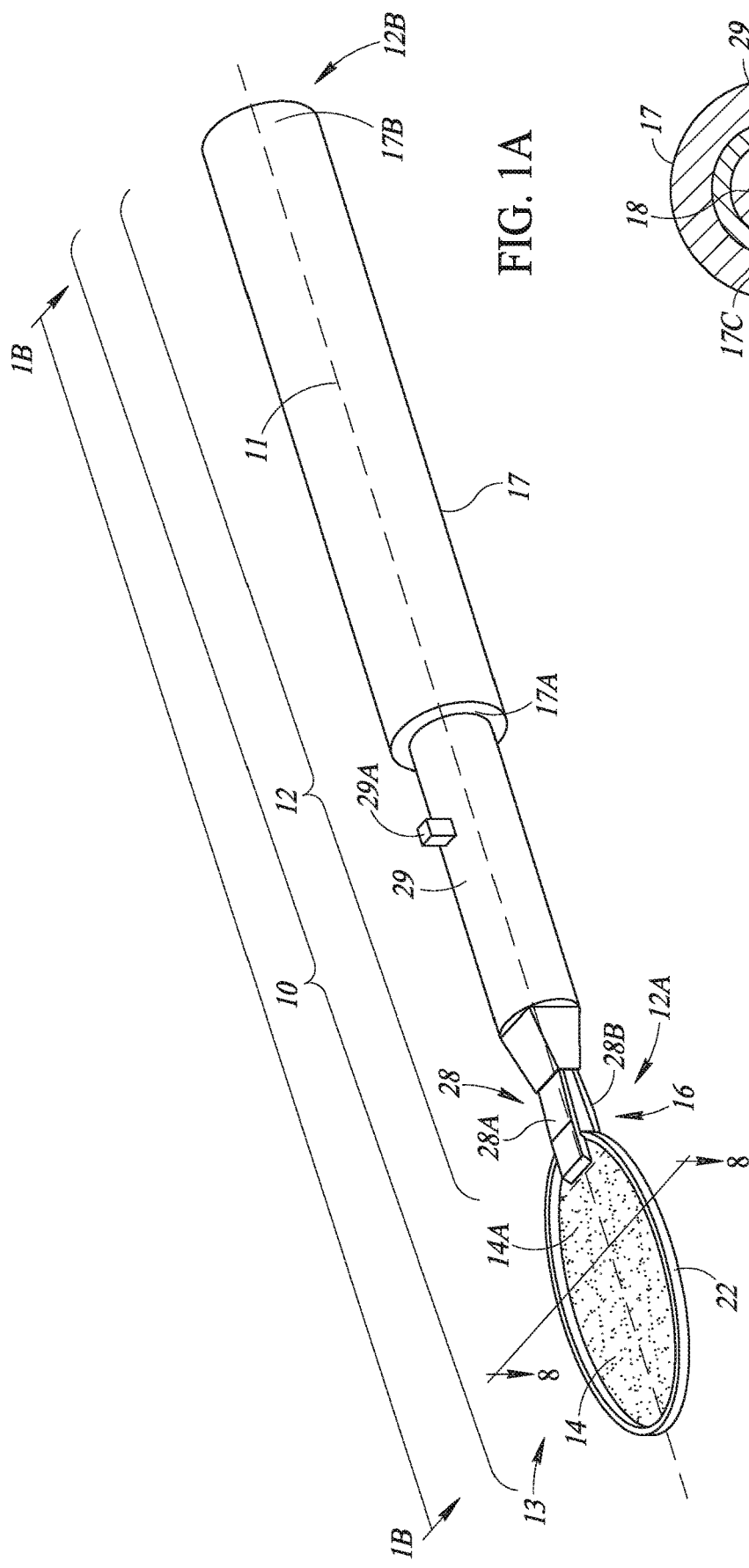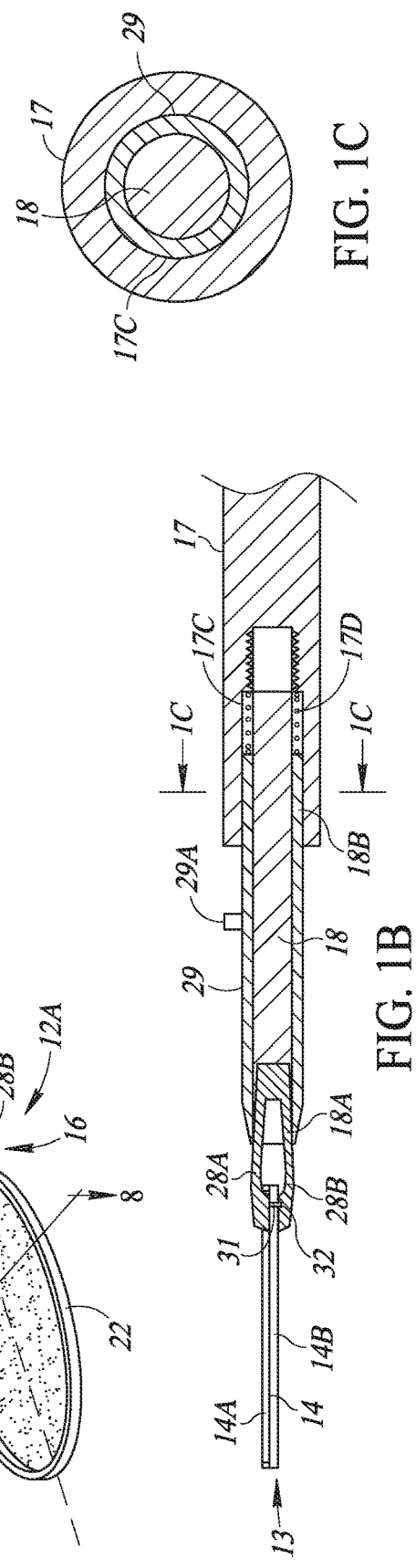

HANDHELD IMPLANTATION DEVICES FOR IMPLANTATION OR RETINAL TISSUE IMPLANT

PRIORITY INFORMATION

The present application is a continuation-in-part of U.S. application Ser. No. 16/501,078, filed on Feb. 19, 2019 (granted as U.S. Pat. No. 11,065,106, issued on Jul. 20, 2021) (which in turn claims priority as a continuing application based on U.S. application Ser. No. 15/111,996, filed on Jul. 15, 2016 (granted as U.S. Pat. No. 10,251,747, issued on Apr. 9, 2019), which claims priority from PCT App. PCT/IL2015/050049, filed on Jan. 14, 2015, and Israeli Patent App. No: 230567, filed on Jan. 21, 2014). The present application is also a National Stage entry of PCT/IL2018/051241, filed on Nov. 18, 2018, which claims priority from Israeli Patent App. No: 255796, filed on Nov. 21, 2017.

FIELD OF THE INVENTION

The invention relates to handheld implantation devices for implantation of retinal tissue implants.

BACKGROUND OF THE INVENTION

The human retina, as in many other vertebrates, has evolved as a layered configuration with an interior retina constituting a neuronal component and an outer retina constituting a light sensing component. The light sensing component is further layered and includes a monolayer of specialized cells known as Retinal Pigment Epithelium (RPE) and a photoreceptor layer. Light entering a human eye passes through a transparent neuronal component before being captured by the photoreceptor layer, transformed to nerve stimuli and sent "backwards" to the neuronal component and from there to the brain. The light sensing component includes over 150 million photoreceptors. The neuronal component organizes the enormous stimuli input to a coded message and converges it to 1.5 million ganglion cells that transfer the coded message to the brain via the optic nerve which is a bundle of all the axons originating from the ganglion cells—one axon per each ganglion cell. The human fovea includes about half of the total number of photoreceptors and is responsible for visual acuity.

Transformation of light photons to nerve stimuli involves biochemical reactions generating large amount of biological waste that must be removed instantaneously and efficiently to maintain uninterrupted visual function. The waste removal is performed by the Retinal Pigment Epithelium (RPE) cells. The apexes of these cells are physically interdigitating with the leading active surfaces of the photoreceptors where the photochemical reactions occur enabling instantaneous removal of the consumed photoreceptor tips and exposure of the segments behind them for further reaction.

Some blinding disorders are caused by pathologic processes largely limited to the outer retina, Such disorders include Age-Related Macular Degeneration (ARMD or AMD) and Retinitis Pigmentosa (RP). Since an inner retina remains functional long after disappearance of a damaged outer retina, vision recovery seems possible by stimulation of a survived inner retina. The concept has been confirmed using electrodes that stimulate an inner retina with electrical pulses. However, the ability to create a sustainable electrobiological interface at the level of organization required for reasonable vision is beyond current knowledge and technology. It was logical to attempt to implant a retinal graft of normal outer-retinal tissue taken from a human cadaver eye or laboratory cultivated from stem cells. Clinical studies conducted over the last decade demonstrate the feasibility of using viable tissue implantation to treat outer retina blinding disorders by encouraging results. However, regardless of the composition of an outer-retinal tissue implant be it human embryonic retinal tissue or laboratory cultivated outer retinal layer tissue, the transfer of such a delicate implant to a human eye has been found to be a major obstacle further emphasized by recent findings that the accurate and stable interface between an outer-retinal tissue implant and a recipient inner retina is a critical factor for successful implantation.

SUMMARY OF THE INVENTION

The present invention is directed toward handheld implantation devices for implantation of retinal tissue implants and in particular outer-retinal tissue implants. The retinal tissue implant can be either full thickness embryonic tissue or partial thickness or full thickness laboratory cultivated tissue. The handheld implantation devices include an elongated handheld implantation tool, an implant holder for peripherally holding a retinal tissue implant, and a clinician-operated attachment arrangement for initial attaching the implant holder to the implantation tool and subsequent detaching the implant holder together with its retinal tissue implant therefrom at an implantation site. Different attachment arrangements can be employed for detachably attaching an implant holder to a handheld implantation tool. In the case of an outer-retinal tissue implant, an implant holder is preferably oval shaped having a major axis between about 6 mm to about 8 mm and a minor axis between about 3 mm to about 5 mm and is intended to be implanted such that its center is implanted at a human eye's fovea.

BRIEF DESCRIPTION OF DRAWINGS

In order to understand the invention and to see how it can be carried out in practice, preferred embodiments will now be described, by way of non-limiting examples only, with reference to the accompanying drawings in which similar parts are likewise numbered, and in which:

FIG. 1A is a front perspective view of an assembled handheld implantation device including a handheld implantation tool and a detachable implant holder peripherally holding an outer-retinal tissue implant in accordance with a first embodiment of the present invention;

FIG. 1B is a longitudinal cross section of the implantation tool along line 1B-1B in FIG. 1A;

FIG. 1C is a transverse cross section of the implantation tool along line 1C-1C in FIG. 1B;

DETAILED DESCRIPTION OF DRAWINGS

Figure 2A:
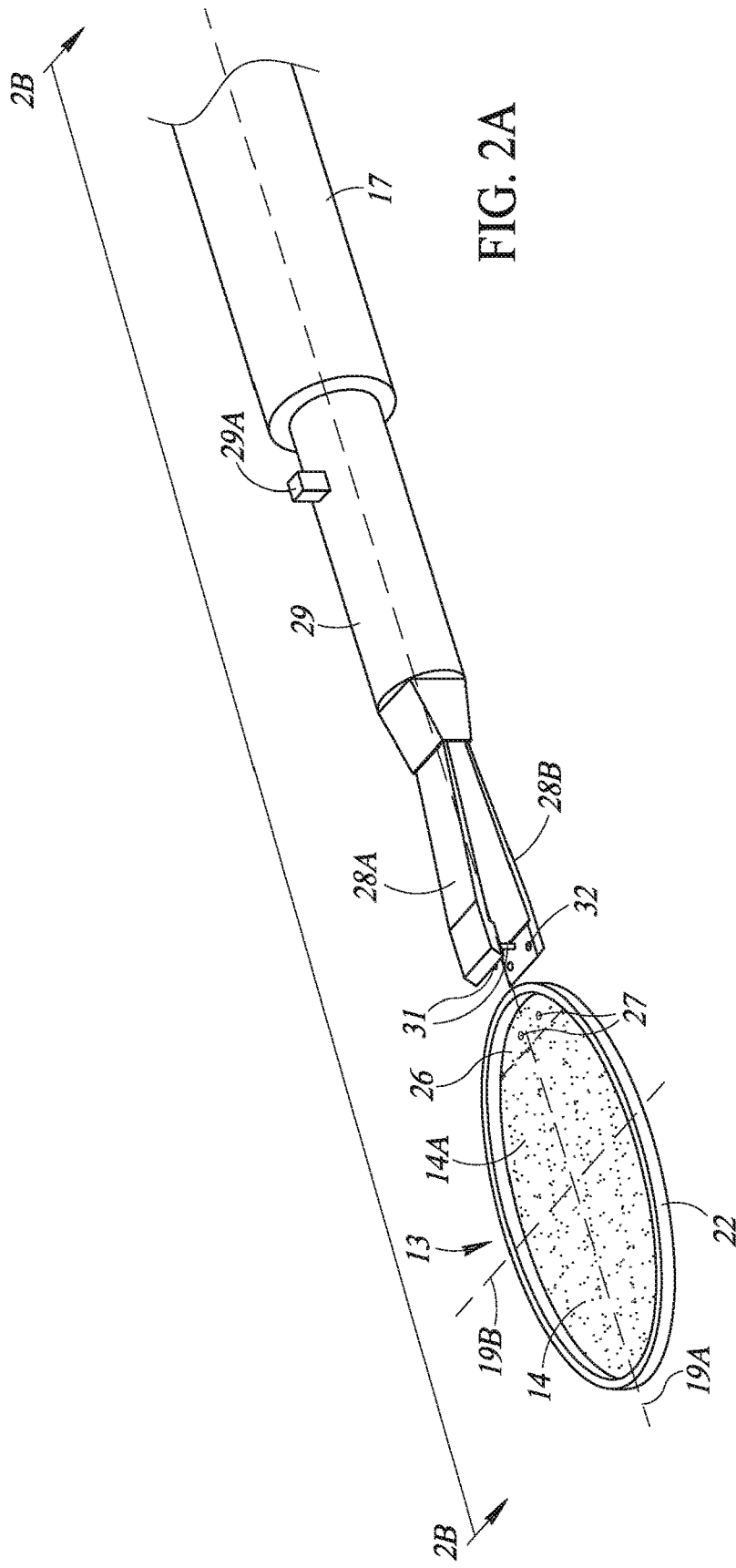
FIG. 2A is a front perspective view of the implantation tool and the implant holder subsequent to detachment of the implant holder therefrom.
Figure 2B:
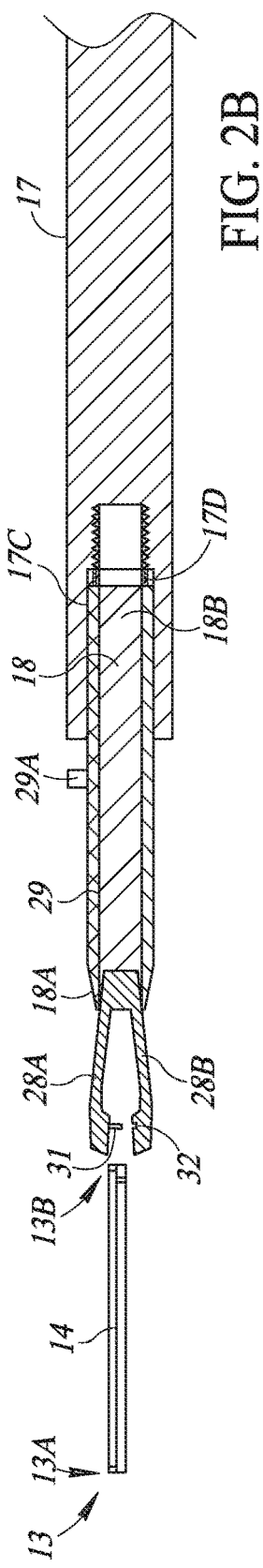
FIG. 2B is a longitudinal cross section of the implantation tool along line 2B-2B in FIG. 2A.
Figure 3:
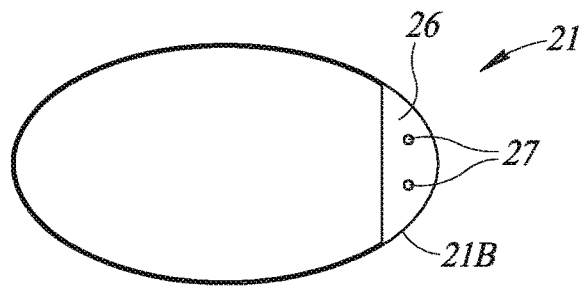
FIG. 3 is a top plan view of an implant carrier of the implant holder.
Figure 4:
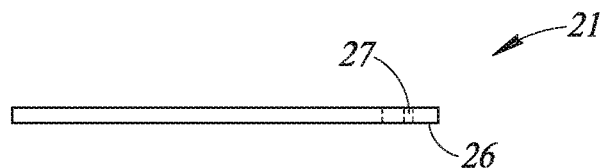
FIG. 4 is a front elevation view of the implant carrier of the implant holder.
Figure 5:
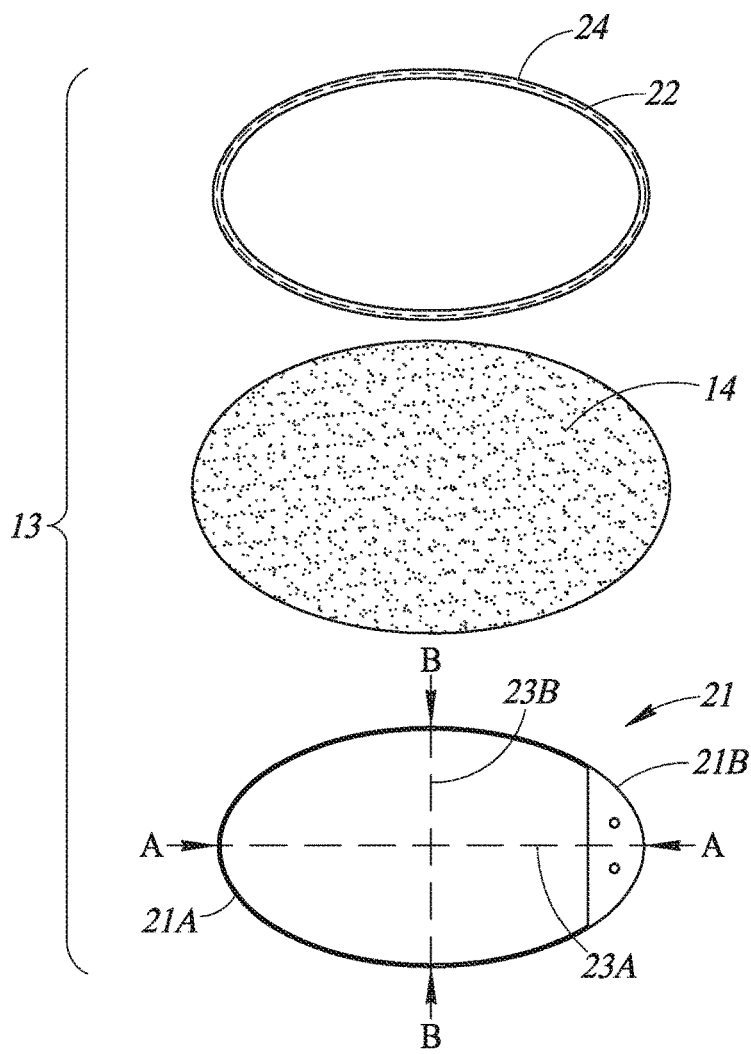
FIG. 5 is an exploded, view of the implant holder including its implant carrier, its outer-retinal tissue implant and its implant carrier surround.

The present invention is described for implanting an outer-retinal tissue implant hereinafter abbreviated as ORTI but can be equally used for implanting other retinal tissue implants. Retinal tissue implants can have a thickness T from between about 15 microns to about 250 microns depending on their intended implantation site, intended therapeutic action, and the like.

FIG. 1 to FIG. 8 show a handheld implantation device 10 has a longitudinal implantation device centerline 11 and includes a handheld implantation tool 12, a generally planar implant holder 13 peripherally holding an ORTI 14 and a releasable clamping arrangement 16 constituting a clinician-operated attachment arrangement for attaching the implant holder 13 to the implantation tool 12 for enabling its selective detachment therefrom together with the ORTI 14 at an implantation site. The handheld implantation tool 12 has a leading implantation tool end 12A and a trailing implantation tool end 12B. The ORTI 14 has uppermost viable retinal tissue 14A and a lowermost basement membrane 14B. The handheld implantation tool 12 includes a handle 17 having a leading handle end 17A and a trailing handle end 17B. The handle 17 has a blind recess 17C extending rearwards from the leading handle end 17A towards the trailing handle end 17B. The blind recess 17C has a transverse circular cross section. The handle 17 supports a shaft 18 inserted into the blind recess 17C for insertion into a recipient's eye through an incision formed in the eye's scleral wall at the pars plana. The shaft 18 has a transverse circular cross section, a leading shaft end 18A and a trailing shaft end 18B at the base of the blind recess 17C The trailing shaft end 18B is screw threaded into the handle 17 or similarly attached thereto.

The implant holder 13 preferably has an oval shape for implanting an ORTI but equally can have other shapes suitable for peripherally holding an ORTI. Accordingly, the implant holder 13 has a major axis 19A co-axial with the longitudinal implantation device centerline 11 defining a leading implant holder end 13A remote from the handheld implantation tool 12 and a trailing implant holder end 13B adjacent the handheld implantation tool 12, and a minor axis 19B. The implant holder 13 includes an implant carrier 21 and a closed implant carrier surround 22 for snugly peripherally mounting on the implant carrier 21 for peripherally holding the ORTI 14 thereon. The implant carrier 21 is manufactured from suitable biocompatible load bearing material, for example, nitinol and the like, having shape memory properties. The implant carrier 21 has a leading implant carrier end 21A and a trailing implant carrier end 21B. The implant carrier 21 is resiliently flexible about a major axis 23A and a minor axis 23B as correspondingly denoted by arrows A and B (see FIG. 5). The implant carrier surround 22 is manufactured from suitable biocompatible resiliently flexible material, for example, silicon, and the like. The implant carrier surround 22 has a generally C-shaped transverse cross section with an internal implant carrier surround groove 24 intended to snugly receive the implant carrier 21 therein thereby peripherally entrapping the ORTI 14, The implant carrier 21 has a segment-like carrier plate 26 at its trailing implant carrier end 21B. The segment-like carrier plate 26 is preferably parallel to the minor axis 23B and distanced therefrom to occupy a relatively small area of the implant carrier 21. The segment-like carrier plate 26 has a spaced apart pair of clamping throughgoing bores 27.

The implantation tool 12 includes a normal open clamping jaw pair 28 at the leading shaft end 18A. The normal open clamping jaw pair 28 includes an uppermost clamping jaw 28A and a lowermost clamping jaw 28B. The implantation tool 12 includes a sleeve 29 mounted on the shaft 18. The sleeve 29 has a transverse peripheral circular cross section for snug sliding displacement in the blind recess 17C. The recess 17C includes a biasing member 17D in the form a compression spring, and the like, for biasing the sleeve 29 to a forward position for urging the normal open clamping jaw pair 28 into a clamping position for clamping on the segment-like carrier plate 26 (see FIG. 1A and FIG. 1B). The sleeve 29 includes a finger grip 29A for urging the sleeve 29 to a rearward position in the recess 17C for compressing the biasing member 1711) thereby enabling the normal open clamping jaw pair 28 to revert to its normal open position for releasing the segment-like carrier plate 26 (see FIG. 2A and FIG. 2B).

The uppermost clamping jaw 28A includes a spaced apart pair of clamping pins 31 for insertion though the spaced apart pair of clamping throughgoing bores 27. The lowermost clamping jaw 28B includes a spaced apart pair of clamping bores 32 for receiving the spaced apart pair of clamping pins 31, The spaced apart pair of clamping pins 31 do not protrude through the spaced apart pair of clamping bores 32 so as not to damage delicate eye tissue on implantation of the implant holder 13. Releasing the clamping arrangement 16 at an implantation site in an implanted eye, leaves the implant holder 13 and the ORTI 14 at the implantation site on withdrawal of the implantation tool 12.

Figure 6:
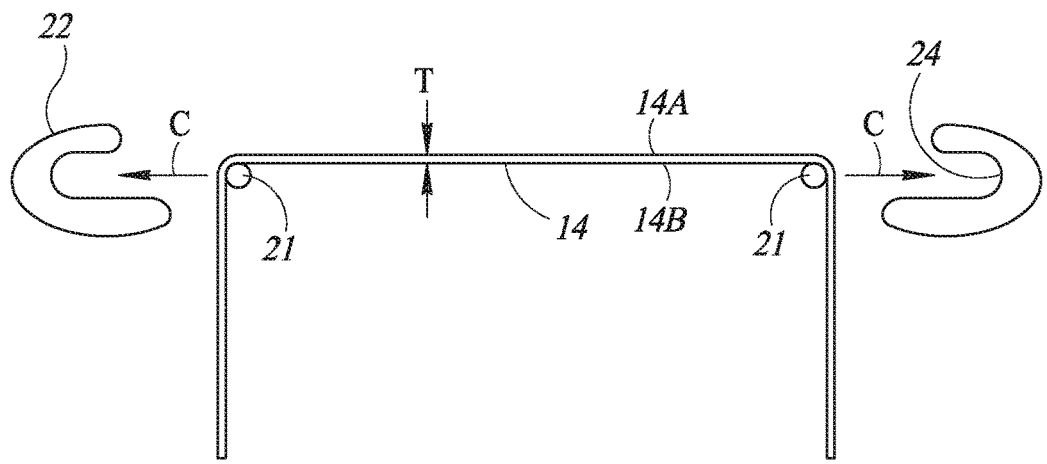
FIG. 6 is a transverse cross section showing an initial step in the preparation of the implant holder.
Figure 7:
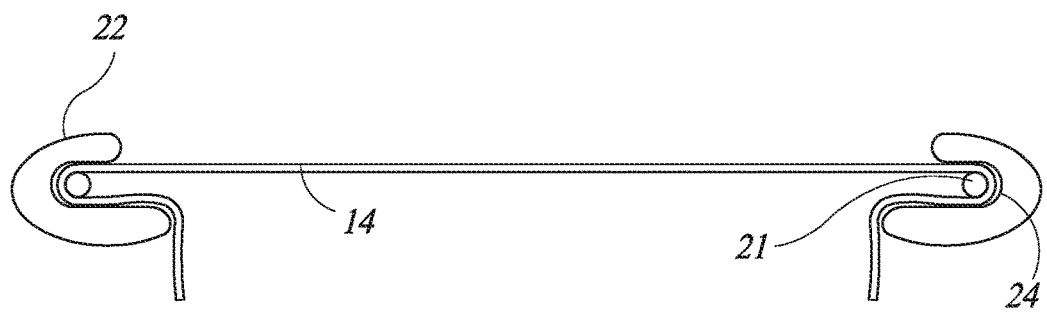
FIG. 7 is a transverse cross section showing the implant holder before trimming the downward depending edge of its outer-retina tissue implant.
Figure 8:
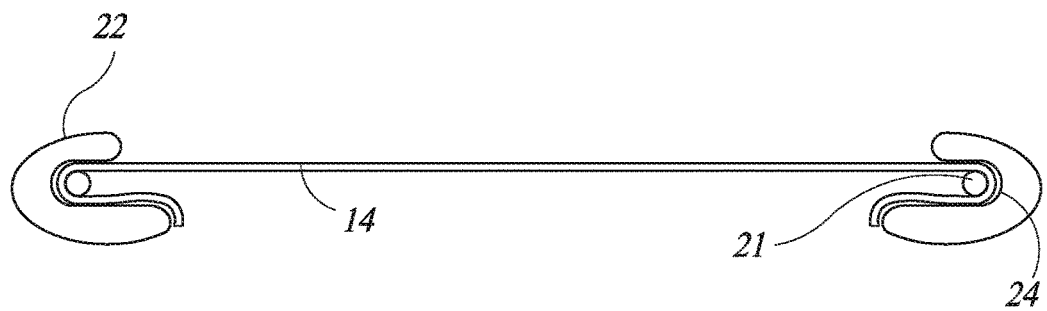
FIG. 8 is a transverse cross section of the implant holder along line 8-8 in FIG. 1A.
Figure 9:
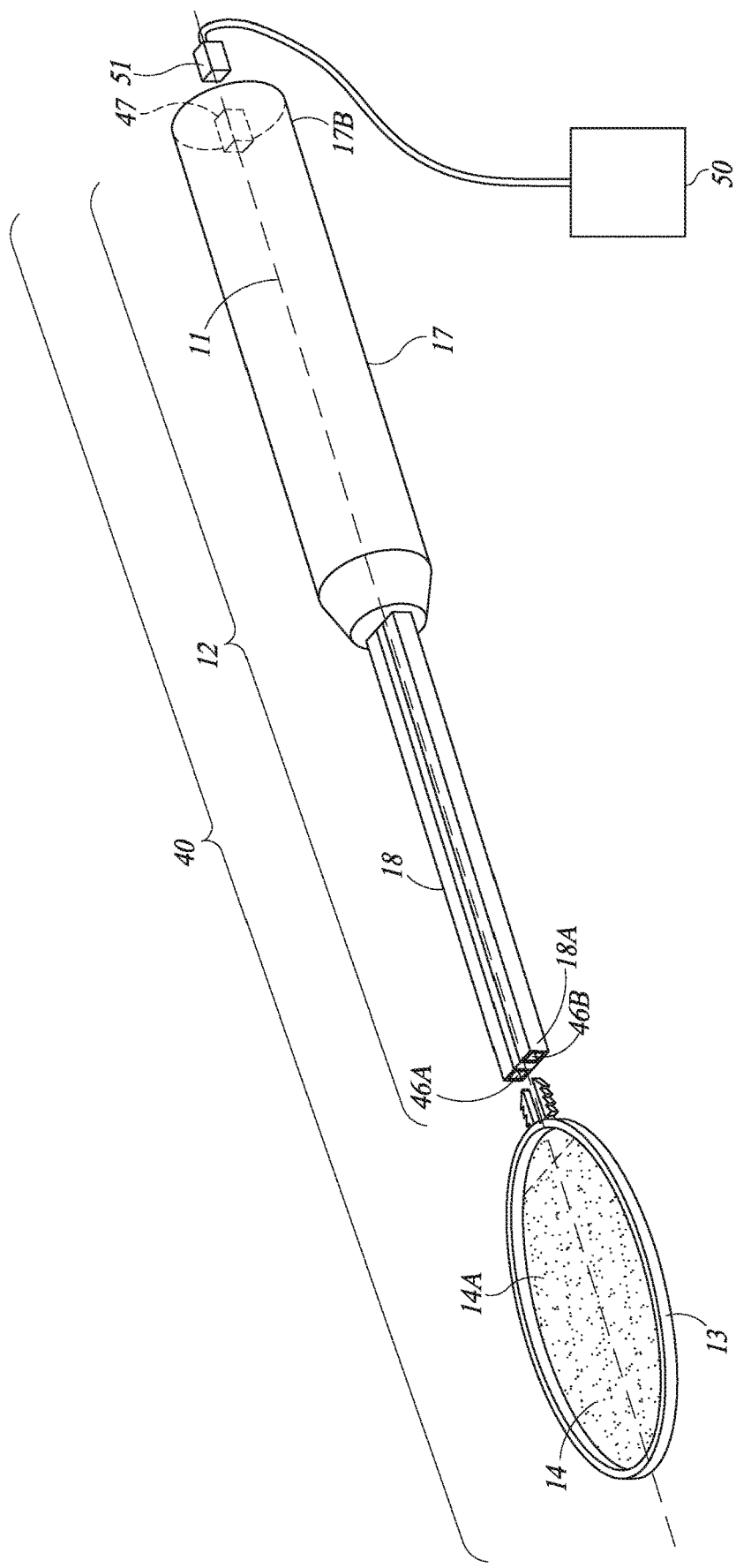
FIG. 9 is a front perspective view of a pre-assembled handheld implantation device including a handheld implantation tool and a detachable implant holder in accordance with a second embodiment of the present invention.
Figure 10:
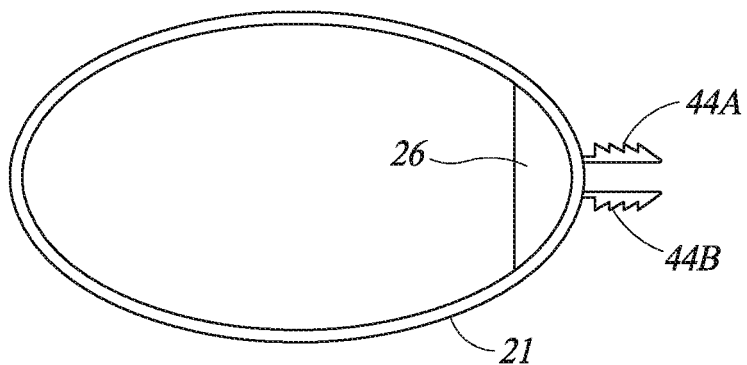
FIG. 10 is a top plan view of an implant carrier of the FIG. 9 implant holder.
Figure 11:
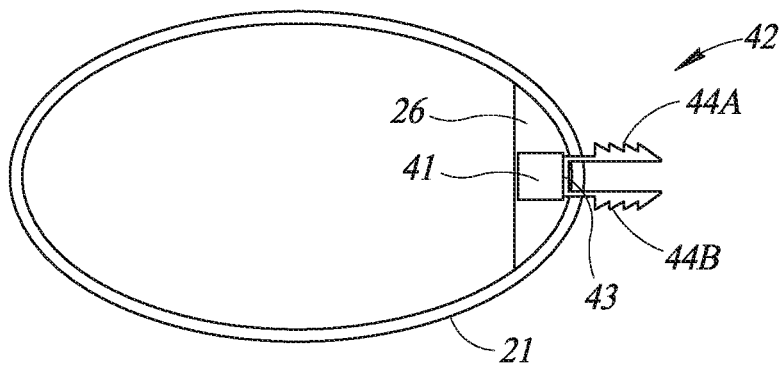
FIG. 11 is a bottom plan view of the implant carrier of the FIG. 9 implant holder.

FIG. 6 to FIG. 8 show preparation of the implant holder 13 as follows: The ORTI 14 is laid on the implant carrier 21 with its lowermost basement membrane 14B resting thereon. The ORTI 14 is typically supplied in the same shape as the implant carrier 21 but larger such that it overhangs the implant carrier 21 to leave a downward depending edge. The ORTI 14 covers the segment-like carrier plate 26. The implant carrier 21 is compressed and is slowly released to entrap the ORTI 14 in the internal implant carrier surround groove 24 as denoted by arrows C (see FIG. 6) such that the ORTI 14 is taut (see FIG. 7). The ORTI 14's downward depending edge is preferably trimmed after securing in the implant holder 13 such that the implant holder 13 presents a streamline profile for implantation purposes (see FIG. 8). On clamping the implant holder 13 in the implantation tool 12, the spaced apart pair of clamping pins 31 traverses the ORTI 14 overlying the segment-like carrier plate 26.

FIG. 9 to FIG. 14 show a handheld implantation device 40 similar to the implantation device 10 and therefore similar parts are likewise numbered. The implantation device 40 is intended for use with a user operated electrical power source 50 having an electrical plug 51. The electrical power source 50 can be operated by a user foot pedal, and the like.

Figure 12:
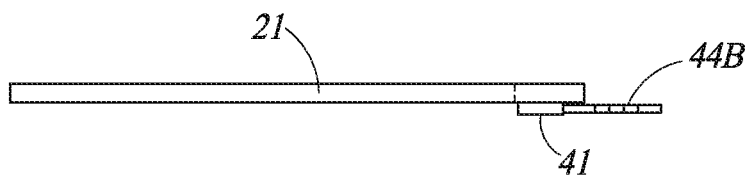
FIG. 12 is a front elevation view of the implant carrier of the FIG. 9 implant holder.
Figure 13:
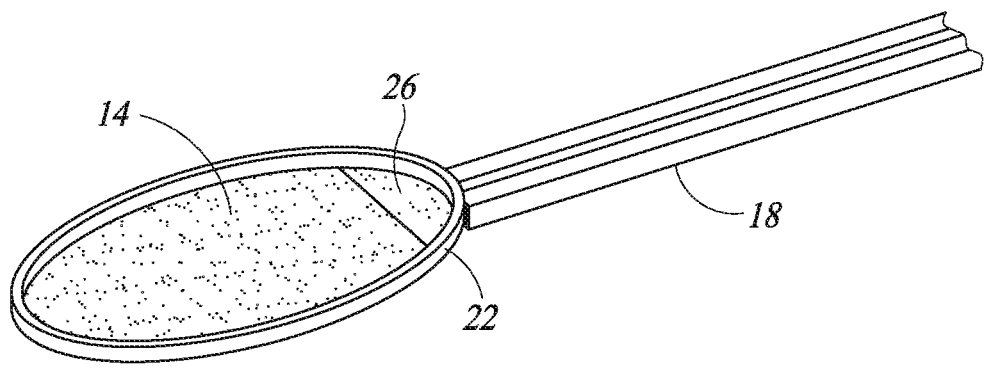
FIG. 13 is a front perspective view of a leading implantation tool end of the implantation tool on attachment of the implant holder thereto.
Figure 14:
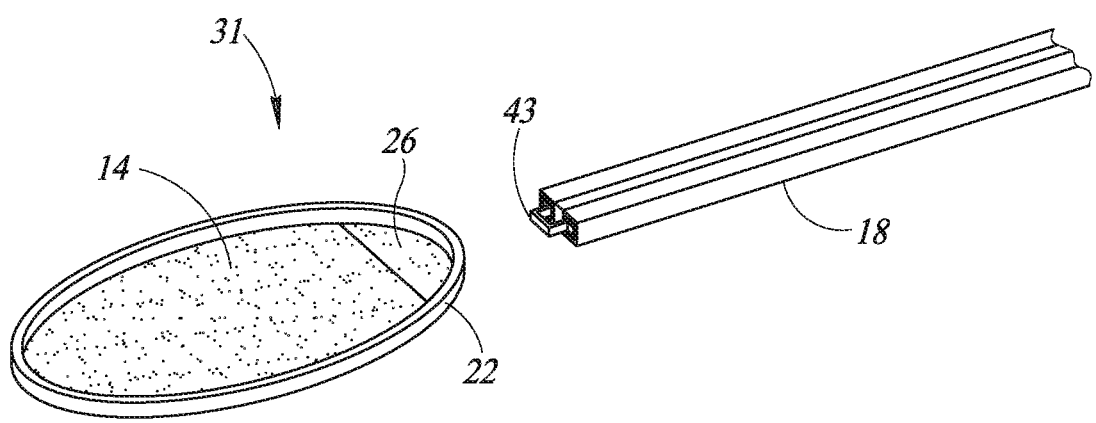
FIG. 14 is a front perspective view of the leading implantation tool end of the implantation tool after detachment of the implant holder therefrom.

The handheld implantation device 40 includes a thermoplastic holding element 41 underlying the segment-like carrier plate 26 in the FIG. 12 front elevation view such that the thermoplastic holding implant 41 faces in the same direction as the lowermost basement membrane 14B. The thermoplastic holding element 41 has a generally U-shaped electrical heating filament 42 including a crosspiece 43 and a spaced apart pair of outwardly protruding connectors 44A and 44B directed away from the leading implant holder end 13A. The crosspiece 43 can be glued or otherwise attached to the thermoplastic holding element 41. The connectors 44A and 44B are preferably barbed. The leading shaft end 18A includes a spaced apart socket pair 46A and 46B for snap fit receiving the spaced apart pair of outwardly protruding connectors 44A and 44B. The spaced apart socket pair 46A and 46B are in electrical connection with an electrical socket 47 at the trailing handle end 17B intended for receiving the electrical plug 51. The electrical heating filament 42 closes an electrical circuit with the electrical power source 50 such that, on activation of the electrical power source 50, the electrical heating filament 42 heats the thermoplastic holding element 41 whereupon the electrical heating filament 42 is detached therefrom. The electrical heating filament 42 remains inserted in the leading shaft end 18A on withdrawal of the implantation tool 12 from an implanted eye leaving the implant holder 13 with its ORTI 14 at an implantation site.

While the invention has been described with respect to a limited number of embodiments, it will be appreciated that many variations, modifications, and other applications of the invention can be made within the scope of the appended claims.

The invention claimed is:

1. A handheld implantation device for implantation of a retinal tissue implant at an implantation site, the handheld implantation device comprising:

(a) a handheld implantation tool having a leading end and a trailing end;
(b) a generally planar and oval-shaped implant holder configured for peripherally holding a retinal tissue implant, said retinal tissue implant including an uppermost viable retinal tissue and a lowermost basement membrane; and
(c) an operator-activated attachment arrangement configured for initial attaching said implant holder at said leading end of said implantation tool, and subsequent detaching said implant holder therefrom when positioned at the implantation site to carry out implantation of said implant holder together with the retinal tissue implant at said implantation site wherein said implant holder includes an implant carrier and a closed implant carrier surround, wherein said closed implant carrier surround includes an internal implant carrier surround groove for snugly receiving said implant carrier therein for peripherally entrapping said retinal tissue implant therebetween.

2. The device according to claim 1, wherein said implant carrier and said segment-like carrier plate are sized and configured to allow the lowermost basement membrane to bear on said implant carrier and said segment-like carrier plate on being peripherally entrapped on said implant carrier by said closed implant carrier surround.

3. The device according to claim 1, wherein said operator-activated attachment arrangement includes a normally open clamping jaw pair and a sleeve slidable thereon between a forward position for clamping said normally open clamping jaw pair on said implant holder and a rearward position for enabling said normally open clamping jaw pair to revert to its normally open position for releasing said implant holder.

4. The device according to claim 3, wherein said handheld implantation tool includes a biasing member for biasing said sleeve into said forward position for clamping said normally open clamping jaw pair on said implant holder.

5. The device according to claim 3, wherein said normally open clamping jaw pair include at least two spaced apart clamping pins for passing through said implant holder in said forward position.

\* \* \* \* \*